United States Patent [19]

Laso

[11] 4,296,103

[45] Oct. 20, 1981

[54] STABILIZED SOLUTION OF CHLORINE OXIDES

[76] Inventor: Felipe Laso, Montecito 59, Mexico City DF, Mexico

[21] Appl. No.: 176,278

[22] Filed: Aug. 8, 1980

[51] Int. Cl.$^3$ .................... A61K 33/40; A61K 33/22; A61K 33/20; A61K 33/02

[52] U.S. Cl. .................................. 424/130; 424/148; 424/149; 424/166

[58] Field of Search .................. 424/148, 149, 130

[56] References Cited

U.S. PATENT DOCUMENTS

| | | | |
|---|---|---|---|
| 2,701,781 | 2/1955 | de Guevara | 424/148 |
| 3,123,521 | 3/1964 | Wentworth et al. | 424/130 |
| 3,147,124 | 9/1964 | Wentworth | 424/149 X |

OTHER PUBLICATIONS

Merck Index, 9th Ed., (1976), entry No. 4691.
Merck Index, 9th Ed., (1976), entry No. 8416.
Merck Index, 9th Ed., (1976), entry No. 7438.

Primary Examiner—Frank Cacciapaglia, Jr.
Attorney, Agent, or Firm—Parmelee, Miller, Welsh & Kratz

[57] ABSTRACT

A stabilized aqueous solution of chlorine oxides containing boron, the solution formed by adding to 1000 parts of water, 4–15 parts by weight of sodium or potassium perborate, and 8–15 parts by weight of sodium peroxide or an equivalent amount of potassium peroxide, hydrogen peroxide, potassium percarbonate or sodium percarbonate, the solution having therapeutic value.

7 Claims, No Drawings

STABILIZED SOLUTION OF CHLORINE OXIDES

BACKGROUND OF THE INVENTION

1. Field of the Invention

The present invention is directed to a stabilized solution of chlorine oxides, and more specifically to a stabilized solution of chlorine oxides containing boron.

2. Prior Art

The stabilization of chlorine dioxide aqueous solutions for use as antiseptics is known, for example, in U.S. Pat. No. 2,701,781, the contents of which are incorporated by reference herein. An inorganic boron compound such as sodium perborate, sodium tetraborate or boric acid is present in such stabilized solutions, and a solution of chlorine dioxide is formed by addition of chlorine dioxide to the inorganic boron compound containing water. Such solutions are described as antiseptic solutions and may contain urea, when used as an oral antiseptic.

The chlorine dioxide stabilized aqueous solutions described in said patent have been suggested for use as a food preservative, for example, in U.S. Pat. No. 3,147,124 wherein such solutions are suggested as a germicide in a cheese making The perborate stabilized aqueous solutions of chlorine dioxide of U.S. Pat. No. 2,701,781 are also discussed in U.S. Pat. No. 3,123,521 wherein sodium carbonate peroxide is substituted for the perborate in formation of stabilized chlorine dioxide solution for use as antiseptic compositions. A reason put forth in substituting for the perborate is that perborate solutions should not be used where boron compounds would tend to accumulate in the digestive systems of humans and, over long periods of time, harmful effects may result.

It has now been found that perborate stabilized aqueous solutions of chlorine oxides can be formed which contain only 4-15 parts by weight of sodium or potassium perborate per liter of water, which, with the addition of a peroxide, such as sodium peroxide or other equivalent oxygen donor such as potassium peroxide, hydrogen peroxide, sodium percarbonate or potassium percarbonate, provides an exceptional orally administrable, ingestible stabilized aqueous solution of chlorine oxides for therapeutic use.

SUMMARY OF THE INVENTION

An orally administrable, ingestible, perborate stabilized aqueous solution of chlorine oxides is prepared by the addition to 1000 parts by weight of water: 80-120 parts by weight sodium or potassium chlorite; 90-130 parts by weight of a 13% aqueous solution of sodium hypochlorite; 5-10 cc of 37.7% hydrochloric acid; 2-4.5 cc of 98.15% sulfuric acid; 4-15 parts by weight of sodium perborate or potassium perborate; 8-15 parts by weight of sodium peroxide or an equivalent amount, based upon an oxygen equivalent basis, of potassium peroxide, hydrogen peroxide, potassium percarbonate or sodium percarbonate. In a preferred solution there is added 6-20 parts by weight urea.

DETAILED DESCRIPTION

The stabilized aqueous solution of chlorine oxides of the present invention are orally administrable, ingestible solutions having therapeutic value, for example in the treatment of amebiasis as disclosed in my copending application Ser. No. 158,649, and in the treatment of burn victims as disclosed in my copending application Ser. No. 158,650, both said applications filed June 12, 1980, and the contents of both said applications being incorporated by reference herein.

The stabilized aqueous solutions of chlorine oxides contain chlorine dioxide as well as other oxides of chlorine. In addition, these solutions must contain a peroxide, percarbonate or other oxygen donor.

In the formation of the stabilized aqueous solution of chlorine oxides, there is added to 900 parts of water 80-120 parts by weight of sodium chlorite or potassium chlorite, and also 90-130 parts by weight of a 13% aqueous solution of sodium hypochlorite, or an equivalent amount by weight of a different strength solution of sodium hypochlorite, or potassium hypochlorite. To this slightly milky-white solution there is added inorganic acids, between about 5-10 cc of 37.7% hydrochloric acid and 2-4.5 cc of 98.15% sulfuric acid which acid is diluted in about 100 ml of water and cooled prior to addition. The acid addition results in a dark red colored solution to which is next added an inorganic perborate.

The inorganic perborate that is used in preparation of the present solution is a perborate selected from sodium perborate and potassium perborate, and is added in an amount of 4-15 parts by weight. Upon addition of the perborate, the solution becomes a pale yellowish color.

An essential ingredient of the present stabilized aqueous solution of chlorine oxides is an oxygen donor such as a peroxide selected from sodium peroxide, potassium peroxide, or hydrogen peroxide, or a percarbonate such as potassium percarbonate or sodium percarbonate. Where sodium peroxide is used, which is preferable, an amount of 8-15 parts by weight is added, while the amount of potassium peroxide, hydrogen peroxide, sodium percarbonate or potassium percarbonate to be added would be an equivalent amount, based on an oxygen equivalent basis, to such an amount of sodium peroxide.

There is also preferably added to the solution 6-20 parts by weight of urea to enhance the palatability of the same.

The additives to the water are added in the above sequence and with stirring. The resultant solution, while it may initially appear to contain a small amount of precipitate, will clarify and become a clear, colorless solution, which has a pH of between about 8-14.5 and a density in the range of 1.08 to 1.095, the pH and density of a particular solution dependent upon the amount and type of the above-defined additives.

EXAMPLE I

As an example of a stabilized aqueous solution of chlorine oxides of the present invention and formation of such a solution, there was added, with continuous stirring during about a 35-minute period, to 900 parts of double distilled water, 105 gm of a 13% by weight aqueous solution of sodium hypochlorite, followed by 90 gm of commercial grade sodium chlorite. To this slightly milky-white solution there was then slowly added a cooled solution of 5.9 cc of 37.7% of hydrochloric acid and 3.05 cc of 98.15% sulfuric acid diluted with 100 ml of water. After addition of the acids, the resultant solution had a dark red color. There was then added 5.0 gm of sodium perborate and a resultant milky yellowish cast appeared in the solution. There was next added 10 gm of sodium peroxide, with the solution turning a cloudy, whitish color which slowly cleared.

Finally, the solution had added thereto 10 gm urea. The final solution was clear and colorless and had a density of 1.08. Prior to the urea addition the pH of the solution is 14.5, while following the addition of the urea a pH of between about 13.5 to 14.0 results.

EXAMPLE II

A further stabilized aqueous chlorine oxide solution was prepared following the procedure of Example I, wherein additional boron was present, by using as the additives to the 900 parts of water the following:

120 gm of a 13% by weight aqueous solution of sodium hypochlorite 95 gm of sodium chlorite 8.9 cc of 37.7% hydrochloric acid, and 3.05 cc of 98.15% sulfuric acid, with these acids diluted with 100 ml distilled water 10.0 gm sodium perborate 10.0 gm sodium peroxide, and 10.0 gm urea.

The resultant clear, colorless solution had a density of 1.09 and a pH of 12.0. A small amount of solids settled which were dissolved upon agitation of the solution.

EXAMPLE III

As a further example of a stabilized solution of chlorine oxides of the present invention and formation of such a solution, there was added, with stirring, to 900 parts of double distilled water 125 gm of a 13% by weight aqueous solution of sodium hypochlorite, followed by 95 gm of sodium chlorite. To this solution there was added a solution of 8.9 cc of 37.7% hydrochloric acid and 3.05 cc of 98.15% sulfuric acid dissolved in cool 100 ml of water. There was then added 15.0 gm of sodium perborate followed by 10.0 gm urea. A slight precipitate formed which was dissolved upon letting the mixture stand for a twenty-four hour period. Next there was added 10.0 gm sodium peroxide. The resultant clear solution had a density of 1.095 and a pH of 8.0.

As indicated above, the stabilized aqueous solutions of chlorine oxides containing boron of the present invention are useful as therapeutic agents in the treatment of amebiasis, burn victims and other disorders.

I claim:

1. A stabilized orally administrable aqueous therapeutic solution of chlorine oxides containing boron prepared by the addition to 1000 parts by weight of water the following:
   80–120 parts by weight of sodium chlorite;
   90–130 parts by weight of a 13% aqueous solution of sodium hypochlorite;
   5–10 cc of 37.7% hydrochloric acid;
   2–4.5 cc of 98.15% sulfuric acid;
   4–15 parts by weight of an inorganic perborate selected from sodium perborate or potassium perborate; and
   8–15 parts by weight of sodium peroxide.

2. A stabilized aqueous solution of chlorine oxides containing boron as defined in claim 1 wherein there is added 6–20 parts by weight of urea.

3. A stabilized aqueous solution of chlorine oxides containing boron as defined in claims 1 or 2 wherein there is substituted for said sodium peroxide an equivalent amount, based on an oxygen equivalent basis, of a peroxide selected from potassium peroxide or hydrogen peroxide.

4. A stabilized aqueous solution of chlorine oxides containing boron as defined in claims 1 or 2 wherein there is substituted for said sodium peroxide an equivalent amount, based on an oxygen equivalent basis, of an inorganic percarbonate selected from sodium percarbonate or potassium percarbonate.

5. A stabilized orally administrable aqueous therapeutic solution of chlorine oxides containing boron, prepared by the addition to 900 parts by weight of water the following:
   105 gm of a 13% by weight aqueous solution of sodium hypochlorite;
   90 gm of sodium chlorite;
   5.9 cc of 37.7% hydrochloric acid, and 3.05 cc of 98.15% sulfuric acid, diluted with 100 ml water;
   5.0 gm sodium perborate;
   10.0 gm sodium peroxide; and
   10.0 gm urea.

6. A stabilized orally administrable aqueous therapeutic solution of chlorine oxides containing boron, prepared by the addition to 900 parts by weight of water the following:
   120 gm of a 13% by weight aqueous solution of sodium hypochlorite;
   95 gm of sodium chlorite;
   8.9 cc of 37.7% hydrochloric acid and 3.05 cc of 98.15% sulfuric acid diluted with 100 ml water;
   10.0 gm sodium perborate;
   10.0 gm sodium peroxide; and
   10.0 gm urea.

7. A stabilized orally administrable aqueous therapeutic solution of chlorine oxides containing boron, prepared by the addition to 900 parts by weight of water the following:
   125 gm of a 13% by weight aqueous solution of sodium hypochlorite;
   95 gm of sodium chlorite;
   8.9 cc of 37.7% hydrochloric acid and 3.05 cc of 98.15% sulfuric acid diluted with 100 ml water;
   15.0 gm sodium perborate;
   10 gm sodium peroxide; and
   10 gm urea.

* * * * *